United States Patent [19]

Grimes

[11] 4,210,155
[45] Jul. 1, 1980

[54] INSPIRATIONAL INHALATION SPIROMETER APPARATUS

[76] Inventor: Jerry Grimes, 1798 N. Garey Ave., Pomona, Calif. 91767

[21] Appl. No.: 930,553

[22] Filed: Aug. 3, 1978

[51] Int. Cl.$^2$ ............................................ A61M 16/00
[52] U.S. Cl. ................................................. 128/727
[58] Field of Search ................... 128/173 R, 193, 194, 128/195, 196, 197, 201, 205, 206, 207, 208, 209, 210, 188, 727, 725, 716, 145.8, 202, 187

[56] References Cited

U.S. PATENT DOCUMENTS

| | | | |
|---|---|---|---|
| 51,002 | 11/1865 | Barnes | 128/728 |
| 393,869 | 12/1888 | Warren | 128/725 |
| 642,149 | 1/1900 | McKenzie | 128/728 |
| 746,380 | 12/1903 | Richardson et al. | 128/205 |
| 853,439 | 5/1907 | Clark | 128/207 |
| 864,908 | 9/1907 | Nebelthan | 128/726 |
| 895,606 | 8/1908 | Warde | 128/726 |
| 2,485,184 | 10/1949 | Blackman et al. | 128/194 |
| 2,647,511 | 8/1953 | Barach | 128/205 |
| 2,829,642 | 4/1958 | DeMelfy | 128/194 |
| 3,086,515 | 4/1963 | Jones | 128/728 |
| 3,097,645 | 7/1963 | Lester | 128/194 |
| 3,467,078 | 9/1969 | Bird et al. | 128/728 |
| 3,559,639 | 2/1971 | Nagus et al. | 128/728 |
| 3,630,196 | 12/1971 | Bird et al. | 128/194 X |
| 3,635,214 | 1/1972 | Rand et al. | 128/208 X |
| 3,821,950 | 7/1972 | Boehringer | 128/728 |
| 3,826,255 | 7/1974 | Hanstad et al. | 128/194 |
| 3,898,987 | 8/1975 | Elam | 128/716 X |
| 3,951,137 | 4/1976 | Conkle et al. | 128/728 |
| 4,061,698 | 12/1977 | Thornwald | 128/194 X |
| 4,094,317 | 6/1978 | Nasnich | 128/194 |
| 4,116,387 | 9/1978 | Kremer, Jr. | 128/194 X |

FOREIGN PATENT DOCUMENTS

| | | | |
|---|---|---|---|
| 181355 | 3/1955 | Austria | 128/188 |
| 2749629 | 5/1978 | Fed. Rep. of Germany | 128/194 |
| 367491 | 8/1908 | France | 128/188 |

*Primary Examiner*—Henry J. Recla
*Attorney, Agent, or Firm*—Fishburn, Gold and Litman

[57] ABSTRACT

A disposable inhalation spirometer apparatus for prophylactic respiratory maneuver is in expensively constructed and intended for single-patient use. The apparatus includes a tube with an interior respiratory passage communicating through a one-way valve structure to a nebulizer assembly and having a separate visual inhalation meter. The nebulizer assembly includes both a medicant mist dispensing nebulizer and an enlarged, enclosed, mist accumulation chamber which is positioned between the nebulizer and the tube passage. The visual inhalation meter includes a tube defining a chamber and having a transparent portion or window with a scale or indicia thereon and in which is mounted a floating piston movable in response to low differential pressure to indicate relative inspirational ability. A one-way check valve in an end of the tube passage opens to the atmosphere upon exhalation and permits the patient to maintain constant contact with a tube mouthpiece.

5 Claims, 4 Drawing Figures

U.S. Patent    Jul. 1, 1980    4,210,155
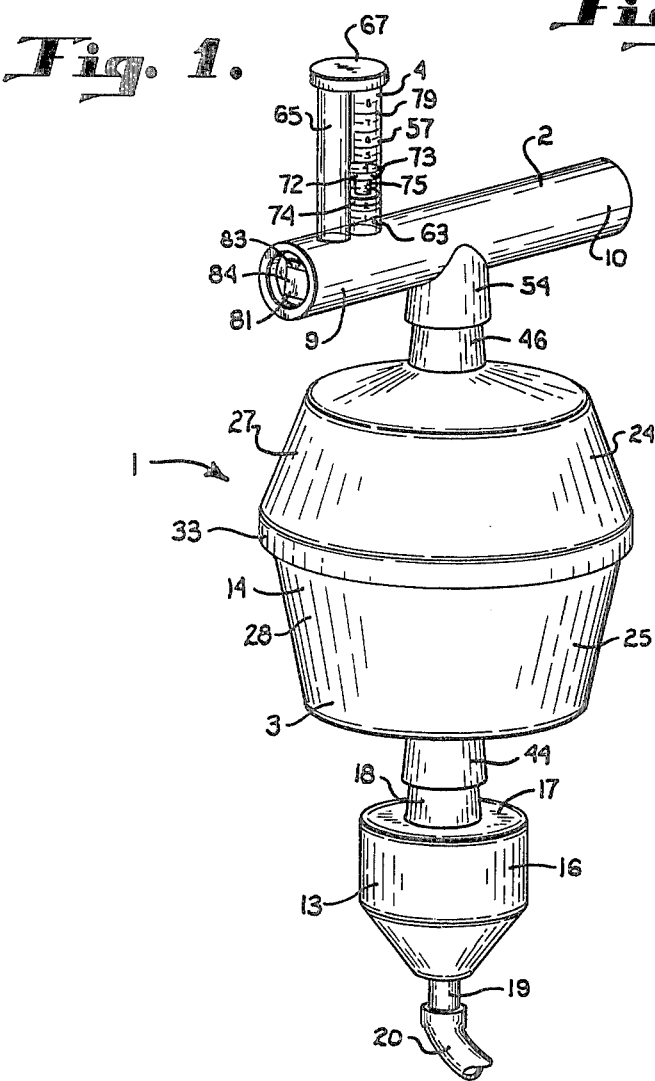
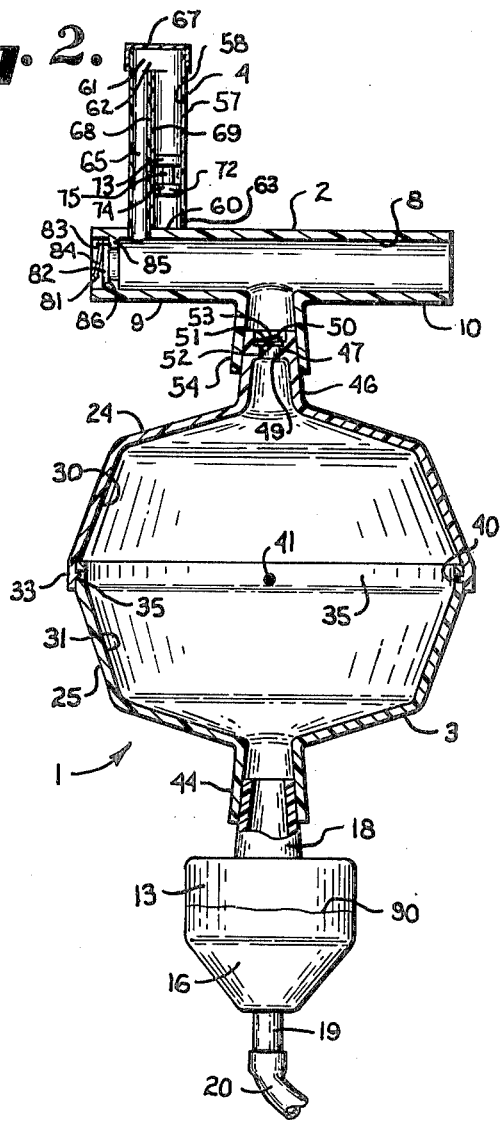
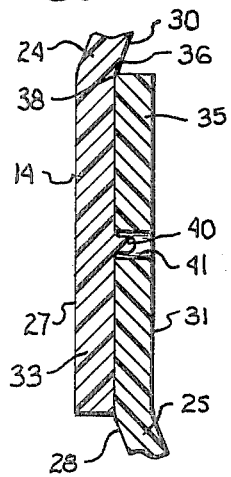
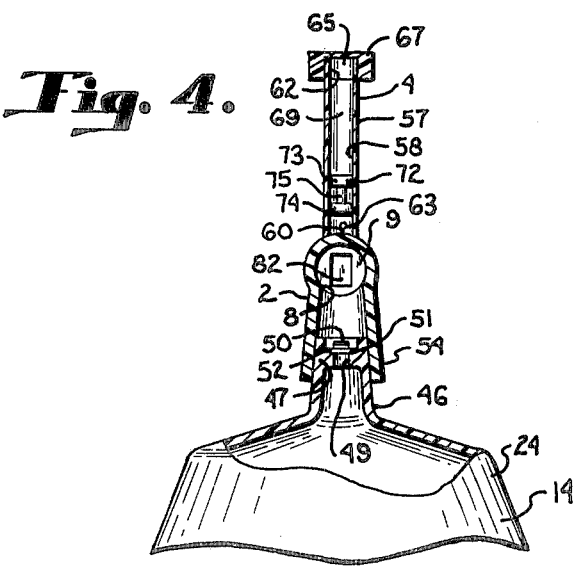

INSPIRATIONAL INHALATION SPIROMETER APPARATUS

This invention relates to an improved prophylactic respiratory device and, in particular, to a disposable, inspirational, combination inhalation spirometer and nebulizer.

In the treatment of respiratory system disorders in patients with either restrictive or obstructive factors, deep breathing exercises with emphasis on sustained inspiration to total lung capacity in combination with inhalation of a therapeutic in aerosol form has consistently been effective in inflating lung alveoli and preventing pulmonary complications. These maneuvers have generally been accomplished under the guidance of physical therapists or by careful patient instruction emphasizing the use of an incentive spirometer. Crucial to chest physical therapy, these exercises have been the mainstay of pulmonary prophylaxsis on many thoracic surgery services and have been effective in preventing atelectasis, or collapse of alveoli, as determined by evaluation of control groups.

Additionally, medicaments such as antihistamines, bronchodilators, vasconstrictors, and antibiotics, plus many others, are often prescribed and commonly administered as an aerosol or mist. To be most effective, the medicant should be inhaled to reach the most remote aleveoli and evenly deposited throughout the patient's airway system. It will be appreciated that the success of this type of therapy depends greatly upon the formation of a proper aerosol or mist and the proper administration thereof. Likewise, the proper administration is dependent upon full lung inflation which is difficult to achieve considering the physical state of the typical patient. Accordingly, a visual measuring means is desired which will indicate to the patient during a prophylactic respiratory maneuver the relative amount of inhaled air and so encourage self-motivated therapy and effective medicant employment.

Regarding the medicational aspect, commonly used nebulizers typically are able to atomize only a small volume of air relative to a typical volume of full inhalation. In view of this, some nebulizers utilize a hand triggering device with which the patient attempts to increase the flow from the nebulizer concurrently with commencing inhalation. When the patient is in a weakened physical condition, this procedure is difficult to perform and as such is unreliable at best in achieving the desired results.

The principal objects of the present invention are: to provide an inhalation spirometer apparatus for prophylactic respiratory maneuver; to provide an inhalation spirometer apparatus which is of sufficiently low cost per unit so as to be disposable and thereby intended for single-patient use; to provide an inhalation spirometer apparatus which includes a medicant mist dispensing nebulizer; to provide an inhalation spirometer apparatus which includes an enlarged, enclosed, mist accumulation chamber for containing the medicated aerosol in sufficient volume to permit the patient to inhale with a minimum effort a sufficient quantity to reach and medicate remote alveoli and airways; to provide an inhalation spirometer apparatus in which an enlarged, enclosed, mist accumulation chamber includes bleed air ports through which additional and ambient air may be drawn if necessary and through which excessive positive atmospheric pressures are relieved; to provide such an inhalation spirometer apparatus including visual meter means indicating relative inspirational ability; to provide such an inhalation spirometer apparatus allowing one to visually monitor therapeutic efforts of the patient; to provide such an inhalation spirometer apparatus including a transparent chamber defining tube and floating piston assembly responsive to low differential pressure which is sensitive to inhalation and indicates same; to provide such an inhalation spirometer apparatus including check valve means whereby a mouthpiece of the apparatus may be retained in the mouth of a patient during both inhalation and exhalation cycles; and to provide such an inhalation spirometer apparatus which is relatively inexpensive, sturdy and efficient in use, and particularly well adapted for the intended purpose.

Other objects and advantages of this invention will become apparent from the following description taken in connection with the accompanying drawings wherein are set forth, by way of illustration and example, certain embodiments of this invention.

FIG. 1 is a perspective view of an inhalation spirometer apparatus embodying the present invention and illustrating nebulizer and visual metering means components thereof.

FIG. 2 is a cross-sectional view of the inhalation spirometer apparatus showing valves thereof in position for inhalation.

FIG. 3 is a fragmentary, cross-sectional view of the connection between respective parts of a mist accumulation chamber positioned between a nebulizer and a respiratory tube of the apparatus.

FIG. 4 is a fragmentary view of a portion of the inhalation spirometer apparatus and showing details thereof.

Referring to the drawings in more detail:

As required, detailed embodiments of the present invention are disclosed herein, however, it is to be understood that the disclosed embodiments are merely exemplary of the invention which may be embodied in various forms, therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally indicates an inspirational inhalation spirometer apparatus embodying the present invention. The apparatus 1 includes a conduit or tube member 2 through which a patient breathes, a nebulizer assembly 3 connected to the tube member 2 for dispensing medicant-laden mist upon inhalation by a patient, and a visual meter means 4 for indicating relative inspirational ability of the patient.

Many suitable materials are available for use in the manufacture of the apparatus 1; however, to present a sanitary and sparkling appearance, it is preferred that the same be formed of a clear synthetic resin material, such as a plastic, which is relatively rigid and sufficiently sturdy for use and which may be readily fabricated. Moreover, it is preferred that the material used, though rigid, be slightly resilient so as not to shatter if dropped upon the floor.

The tube member 2 forms a conduit having an interior passage 8 and opposite end portions 9 and 10. The end portion 10 may be connected to structure facilitating breathing through the apparatus 1, such as a mask, mouthpiece, or the like (not shown) for use by a patient.

The nebulizer assembly 3 includes a mist-dispensing nebulizer 13 which communicates with an enlarged, enclosed, mist accumulation chamber 14 that in turn, communicates with the tube interior passage 8. Virtually any type of effective nebulizer 13 may be employed with the present invention and in the illustrated example, a nebulizer 13, such as disclosed in U.S. Pat. No. 3,097,645, is utilized. The nebulizer 13 includes a bowl 16 of which the lower portion narrowens downwardly relative to a comparatively broad upper portion. A cover 17 engages over the bowl 16 and has an aerosol or mist exit fitting 18 which is tapered and fits into a commensurately shaped inlet 44 of the mist accumulation chamber 14, described below.

An inlet nozzle 19 extends outwardly from a bottom of the bowl 16 and admits a carrier gas, such as compressed air or oxygen, which is connected via a flexible hose 20, or some other suitable means, to the source of such gas. Preferably, to fill the mist accumulation chamber 14, the gas source (not shown) directs gas, such as air, or oxygen at a slight positive pressure of approximately 15 psi to the inhalation spirometer apparatus 1 at a rate of about 2 to 10 liters per minute. Accordingly, where a hospital oxygen supply system is used which may deliver gas at 50 psi, step-down valving means may be necessary to reduce the pressure to a desired 15 psi. However, it is not necessary that gas be delivered at a positive pressure and ambient air may be drawn directly through the air inlet nozzle 19.

The mist accumulation chamber 14 includes a pair of rigid, upper and lower, paired, bowl-like sections 24 and 25 connected together to form a substantially spherical chamber and having respective smooth outer surfaces 27 and 28 and inner surfaces 30 and 31.

The accumulation chamber upper section 24 has a lower edge or rim 33 extending therearound and the lower section 25 has an upper edge or rim 35 which engages loosely with the rim 33 to permit the passage of air through the connection. In the illustrated example, FIG. 3, the upper section lower rim 33 is slightly greater in diameter than the upper rim 35 of the lower section 25 and both rims 33 and 35 are parallely aligned to slide smoothly together in overlapping relationship. The juncture of the rim 33 with the remainder of the upper section 24 forms an interior shoulder 36 which serves as a stop to limit intrusion of a corner 38 of the upper rim 35 of the lower section 25.

In the illustrated example, connection of the bowl-like upper and lower sections 24 and 25 is effected by a plurality of pairs of mating protuberances or lugs 40 and apertures 41 of slightly larger size than the protuberances or lugs 40 for a loose connection therearound. It will be appreciated that, though substantially rigid, the resiliency of the preferred material of manufacture permits the lower and upper rims 33 and 35, upon parallel alignment thereof, to be pushed together and effect a snap fit between the protuberances or lugs 40 and the apertures 41. Moreover, a relatively loose fit or connection is effected which, in combination with the larger size of the apertures 41 relative to the protuberances or lugs 40, permits the apertures 41 to act as vents or bleed air ports between the mist accumulation chamber 14 and the exterior atmosphere in which air or gas moves through the apertures 41 and outwardly between the overlapping rims 33 and 35.

Preferably, the mist accumulation chamber 14 is of sufficient size to enclose approximately 700 milliliters of volume; this size is deemed sufficient in most uses and comprises a normal full inhalation for an average patient. It is recognized that a 700 milliliter volume chamber 14 represents a compromise construction which normally permits a patient to inhale a full breath and yet which is not overly bulky in size. However, provision has been made for admission of ambient air into the mist accumulation chamber 14 in the event that the patient takes a sufficiently deep breath to empty accumulated aerosol or mist within the chamber 14. In the illustrated example, the relatively loose snap-fit between the rims 33 and 35 and between the protuberances or lugs 40 and the apertures 41 creates bleed air lines and ports through which ambient air or gas is sucked during under pressure conditions. Alternatively, in an instance wherein an air or gas source is connected to the air inlet nozzle 19 via the hose 20 and builds up significant overpressure within the mist accumulation chamber 14, the loose connection between the rims 33 and 35 and the bleed air ports permit escape of such overpressure air from the chamber 14 and maintain only a slight positive pressure within the chamber 14.

As previously described, the mist accumulation chamber 14 is positioned between the tube member 2 and the nebulizer 13. Extending outwardly from the lower section 25, preferably at the lowest area thereof, is a circular nozzle or inlet 44 which tapers or expands outwardly and is of commensurate size to snugly receive the coordinatingly tapered nebulizer tube 18 and thereby provide a snug, leak-free, easily disconnectable, press fit.

Providing connecting means between the mist accumulation chamber 14 to the tube member 2, the bowl-like upper section 24, preferably at the apex area thereof, includes an upwardly extending nozzle or outlet 46 which tapers upwardly in diameter. In the illustrated example, the outlet 46 includes a shoulder member 47 which surrounds and defines a throughbore 49. Spanning the upper side of the shoulder member 47 and across the throughbore 49 is a valve means 50 which preferentially effects closure of the throughbore 49. In the embodiment shown, the valve means 50 includes a resilient, planar flapper 51 which moves downwardly and into sealing engagement with a valve seat 52 in the shoulder member 47.

It will be appreciated that the valve means 50 comprises a one-way check valve which opens because of suction effect upon inhalation and permits medicant laden aerosol or mist to be evacuated from the mist accumulation chamber 14 and pass through the tube member 2 and into the lungs of the patient. The flapper 51 is biased to a seating position and upon exhalation, the flapper 51 is forced downwardly from the force of air pressure and tightly seals against the valve seat 52 and thereby closes the mist accumulation chamber 14.

The medicant laden air or gas may be under pressure within the mist accumulation chamber 14 as described above. It will be appreciated that upon passage from the nebulizer 13 and into the chamber 14, the air or gas expands with a commensurate drop in pressure to such a pressure which is not sufficient to open the valve means 50. The rate of gas flow may have to be adjusted to maintain this condition.

Permitting connection of the tapered outlet 46 to the tube member 2, the latter includes a downwardly extending nozzle or inlet 54 which tapers outwardly and increases in diameter and is of commensurate size and configuration to snugly receive the outlet 46 in press fit engagement.

Positioned closer to the tube end portion 9 than the inlet 54 for the nebulizer assembly 3, or upstream thereof, is the visual meter means 4 which indicates relative inhalational ability. In the illustrated example, the visual meter means 4 includes a transparent tube 57 that defines a cylindrical inner chamber 58 having a closed bottom portion 60 with a bleed or vent port 63 extending through the wall of the tube 57 and an open top portion 61. The open top portion 61 includes a passage 62 communicating with a conduit or tube 65 which in turn, opens to the interior passage 8 of the tube member 2. The tubes 65 and 57 are in parallel or side-by-side relationship, and jointly have a cover or cap 67 snugly fitting over the upper adjoining ends thereof and sealing same from the exterior atmosphere.

Accordingly, the respective adjoining walls 68 and 69 of the tubes 65 and 67 terminate at the upper end thereof short of the cover or cap 67 and thereby form the passage 62 between the tubes 57 and 65. It will be appreciated that suction pressures effected by inhalation from the tube end portion 10 are communicated to the tube 57 through the tube 65 which transfers the pressures to the upper or open top portion 61 of the tube 57.

Slidably mounted within the tube 57 is a float or piston 72 responsive to low differential pressure which includes upper and lower sealing rings 73 and 74 and a tubular body 75 extending therebetween.

Preferably, a scale or indicia 79 is marked on the exterior surface of the visual meter means 4 and indicates the extent of upward travel of the float or piston 72 upon inhalation by the patient. Additionally, upper portions of the float or piston 72 may be color coded so the patient may determine at a glance the extent of upward travel of the float or piston 72 within the tube 57. Furthermore, the float or piston 72 may be itself be color coded and formed of a material having, for example, a reddish tinge so as to merge upon upward travel with portions of the meter means 4 having, for example, a reddish tinge and thereby provide readily apparent visual indications and simple incentive or inspiration during therapeutic maneuver.

Closing the tube end portion 9 is a valve means 81 comprising, in the illustrated example, a one-way check valve similar in construction to the valve means 50 between the mist accumulation chamber 14 and the tube member 2. Accordingly, the valve means 81 includes a resilient, relatively flexible tab or flapper 82 connected at an end 83 to an interior shoulder 85 within the end portion 9. A valve seat 86 in the interior shoulder 85 provides a sealing surface upon closure of the flapper 82 during inhalation by a patient. The valve means 81 is biased toward a seating position and is closed to the atmosphere exterior of the spirometer apparatus 1 during inhalation and open thereto upon exhalation by the patient, thereby permitting the user to maintain contact with the spirometer apparatus 1 during both inhalation and exhalation cycles.

In operation of the inhalation spirometer apparatus 1, the nebulizer 13 is filled with a liquid therapeutic 90 to a desired level and an air bulb (not shown) or any other suitable source of compressed air, oxygen or other desired gaseous fluid connected to the nozzle 19 by a suitable conduit or hose 20. Alternatively, a hose 20 need not be connected to the nozzle 19 and ambient air may be drawn therethrough. The patient may then utilize the tube end portion 10 as a mouthpiece or the end portion 10 may be attached to a mask (not shown) covering the patient's face.

As the air courses upwardly through the nebulizer 13, a fine medicant-laden aerosol or mist is produced which exits through the tube 18 and accumulates within the chamber 14. The amount accumulated depends, of course, upon the size of the chamber 14; where a chamber 14 of 700 milliliters volume is employed, a commensurate volume of aerosol or mist accumulates. As described above, the relatively loose connection between the upper and lower section rims 33 and 35 and the bleed ports or apertures 41 permit passage of ambient air should the aerosol accumulation in the chamber 14 be insufficient or should a particular air source attempt to create a significant overpressure within the chamber 14.

Upon inhalation by a patient, the valve means 50 opens and the valve means 81 closes and creates a suction within the spirometer apparatus 1 which draws the medicant-laden mist from the chamber 14, through the tube passage 8 and into the patient's airways and lungs.

Additionally, relative inhalational effort and capacity are indicated on the visual meter means 4. Simultaneously with drawing medicant-laden aerosol or mist from the chamber 14, negative pressure in the tube passage 8 is transferred upwardly through the tube 65 and the passage 62 and into the cylindrical chamber 58 of the tube 57. In response, the float or piston 72 is drawn upwardly within the chamber 58 and indicates relative inhalational effort. For example, where the float or piston 72 and portions of the scale indicia 79 are color coded red, a therapist supervising a deep breathing exercise using the inhalation spirometer apparatus 1 may direct the patient to "put red on red," meaning the patient should attempt to inhale sufficiently deeply to pull the float or piston 72 into the upper part of the chamber 58.

Upon reaching the peak of the inhalation cycle, the float or piston 72 will begin to fall gradually toward the closed portion bottom 60 of the tube 57 in preparation for the next inhalation cycle. Additionally, exhalation pressrues passing through the spirometer apparatus 1 are communicated to the upper sealing ring 73 of the float or piston 72 and in response thereto the piston moves downwardly within the chamber 58. The vent port 63 facilitates movement of the float or piston 72 within the chamber 58 relative to the closed bottom portion 60 by permitting a slight amount of air to pass therethrough and prevent both a suction upon inhalation and a cushion effect during exhalation.

Upon exhalation, concurrently with downward movement of the float or piston 72, the flapper 82 of the valve means 81 opens and allows venting of the air into the atmosphere.

It will be appreciated that the spirometer apparatus 1 is relatively easy for a patient to handle and is balanced to prevent spilling of the therapeutic liquid 90 contained within the nebulizer 13. The main portion of the weight of the spirometer apparatus 1 lies in the nebulizer assembly 3 which is downward of the visual meter means 4 and thereby maintains the latter in an upright position for proper function.

It is to be understood that while one form of this invention has been illustrated and described, it is not to be limited to the specific form or arrangement of parts herein described and shown except insofar as such limitations are included in the following claims.

What is claimed and desired to secure by Letters Patent is:

1. A disposable inhalation spirometer apparatus for prophylactic respiratory maneuver and intended for single patient use, said spirometer apparatus comprising:

(a) a tube member having an interior respiratory passage and opposite end portions, one of said end portions having means for breathing use by a patient;

(b) an enlarged, enclosed mist accumulation chamber of substantially greater cross-sectional diameter than said tube member and of a size to contain a volume of air on the order of an entire inhalation by the patient and having a rigid wall and inlet means and an outlet means connected closely adjacent to said tube member interior passage intermediate said opposite end portions;

(c) a bleed port extended through said wall and open to the atmosphere exterior of said accumulation chamber;

(d) a medicant mist dispensing nebulizer having outlet means connected to said accumulation chamber inlet means whereby an entire inhalation of air and medicant is collected in said accumulation chamber and having a nebulizer inlet means communicating with a pressurized gas supply source for introducing a flow of pressurized gas in said spirometer apparatus;

(e) check valve means positioned between said chamber and said tube member and operative to close automatically upon expiration and open upon inhalation;

(f) a visual meter indicating relative inhalational ability and including a tube having a transparent portion and defining a meter chamber connected to and extended upwardly from said tube member and positioned closer to the other end portion of said tube member relative to said accumulation chamber, said meter chamber having a substantially closed bottom and a top communicating with a passage to said tube member and directing respiratory pressure differentials thereto;

(g) a piston responsive to said respiratory pressure differentials slidably mounted in said meter chamber and moving upwardly therein upon inhalation and moving downwardly therein upon exhalation by said patient; and (h) check valve means at the other end portion of said tube member and operative to close automatically upon inhalation and open upon exhalation, said visual meter positioned between said check valve means at the other end portion and said accumulation chamber outlet means.

2. A disposable, lightweight, compact inhalation spirometer apparatus for prophylactic respiratory maneuver and intended for single patient use, said spirometer apparatus comprising:

(a) an air inlet tube having an interior passage and opposite end portions, one of said end portions including means adapted for connection to means providing a flow of pressurized air for breathing by a patient;

(b) the other end portion of said air inlet tube connected to a nebulizer having a medicant fluid reservoir therewith, said nebulizer having an outlet and a mist dispensing nozzle communicating with said air inlet tube and receiving the flow of pressurized air therethrough;

(c) an enlarged, enclosed mist accumulation chamber having an inlet and outlet and a rigid wall therearound and having said inlet connected to said nebulizer outlet, said mist accumulation chamber being of substantially greater cross-sectional area than said air inlet tube and of a size to collect and contain a volume of air and medicant mist on the order of an entire inhalation of air and medicant mist by said patient;

(d) a breathing tube having an interior passage, one end including means for breathing therethrough by the patient and a second end for exhalation of expired air, said outlet of said mist accumulation chamber connected to said breathing tube intermediate of said one end and said second end for supplying air and medicant mist to said patient upon inhalation;

(e) a visual meter means affixed to said breathing tube adjacent said mist accumulation chamber outlet and operative therewith to provide an indication of breathing ability, said meter means having a float slidably positioned in a tubular housing and sensitive to pressure differentials in said breathing tube to move up and down in said housing; and (f) a valve means communicating with said breathing tube to prevent flow from said mist accumulation chamber and permit flow through said second end upon exhalation and permit flow from said mist accumulation chamber and prevent flow through said second end upon inhalation.

3. The spirometer apparatus as set forth in claim 2 wherein:

(a) said mist accumulation chamber includes a bleed air port extended through said wall and open to atmosphere exterior thereof for venting excessive pressure therefrom.

4. The spirometer apparatus set forth in claim 2 wherein:

(a) said check valve means are positioned between said mist accumulation chamber and said breathing tube and responsive to differential pressure and opening upon inhalation.

5. The spirometer apparatus set forth in claim 2 wherein:

(a) said visual meter means includes said tubular housing upstanding from said breathing tube and a second tube upstanding therewith and having an internal passage communicating with said float to move said float upwardly in said tubular housing in response to inhalation by said patient.

* * * * *